(12) United States Patent
Chauhan et al.

(10) Patent No.: US 8,071,121 B2
(45) Date of Patent: *Dec. 6, 2011

(54) DISPERSIONS OF MICROEMULSIONS IN HYDROGELS FOR DRUG DELIVERY

(75) Inventors: Anuj Chauhan, Gainesville, FL (US); Derya Gulsen Onbilger, Midlothian, VA (US); Yash Kapoor, Gainesville, FL (US); Chi-Chung Li, Lansdale, PA (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 1127 days.

This patent is subject to a terminal disclaimer.

(21) Appl. No.: 11/896,571

(22) Filed: Sep. 4, 2007

(65) Prior Publication Data

US 2008/0075757 A1 Mar. 27, 2008

Related U.S. Application Data

(63) Continuation-in-part of application No. 10/802,058, filed on Mar. 17, 2004, which is a continuation-in-part of application No. 10/454,836, filed on Jun. 5, 2003, now Pat. No. 7,638,137.

(60) Provisional application No. 60/385,571, filed on Jun. 5, 2002.

(51) Int. Cl.
*A61K 9/113* (2006.01)
(52) U.S. Cl. ....................................... 424/429
(58) Field of Classification Search ................. None
See application file for complete search history.

(56) References Cited

U.S. PATENT DOCUMENTS

| 4,484,922 | A | 11/1984 | Rosenwald |
| 4,668,506 | A | 5/1987 | Bawa |
| 5,723,131 | A | 3/1998 | Schultz et al. |
| 6,027,745 | A | 2/2000 | Nakada et al. |
| 6,221,399 | B1 | 4/2001 | Rolfes |
| 6,410,045 | B1 | 6/2002 | Schultz et al. |
| 7,638,137 | B2 * | 12/2009 | Chauhan et al. ............ 424/429 |
| 2004/0241207 | A1 | 12/2004 | Chauhan |

OTHER PUBLICATIONS

Nagarsenker, M.S., Londhe, V.Y., Nadkarni, G.D., "*Preparation and evaluation of liposomal formulations of tropicamide for ocular delivery*", Int. J. of Pharm., 1990, 190: 63-71.
Lang, J.C., "*Ocular drug delivery conventional ocular formulations*". Adv. Drug Delivery, 1995, 16: 39-43.
Bourlais, C.L., Acar, L., Zia H., Sado, P.A., Needham, T., Leverge, R., "*Ophthalmic drug delivery systems*", Progress in retinal and eye research, 1998, 17, 1: 33-58.
Segal, M., "*Patches, pumps and timed release*", FDA *Consumer* magazine, Oct. 1991.

(Continued)

*Primary Examiner* — Carlos Azpuru
(74) *Attorney, Agent, or Firm* — Miles & Stockbridge P.C.; David R. Schaffer, Esq.

(57) ABSTRACT

An ophthalmically bioactive agent delivery system comprising a contact lens having dispersed therein as an oil-in-water microemulsion, an ophthalmically bioactive agent encapsulated in the oil phase, the oil phase comprising a material from which the agent VAN diffuse into and migrate through the contact lens into the post-lens tear film when the contact lens is placed on the eye and wherein the microemulsion is stabilized by the presence of a surfactant with sufficient packing at the oil-water interface to attenuate the rate of diffusion into and migration of agent through the contact lens.

6 Claims, 9 Drawing Sheets

OTHER PUBLICATIONS

Hehl, E.M., Beck, R., Luthard K., Guthoff R., "*Improved penetration of aminoglycosides and fluoroquinolones into the aqueous humour of patients by means of Acuvue contact lenses*", European Journal of Clinical Pharmacology, 1999, 55 (4): 317-323.

Hillman, J. S., "Management of acute glaucoma with Pilocarpine-soaked hydrophilic lens" Brit. J. Ophthal.58 (1974) p. 674-679.

Ramer, R. and Gasset, A., "Ocular Penetration of Pilocarpine:" Ann. Ophthalmol.6, (1974) p. 1325-1327.

Montague Ruben and Watkins, Robert., "Pilocarpine dispensation for the soft hydrophilic contact lens" Brit. J. Ophthal. 59, (1975) p. 455-458.

Hillman, J.,Marsters, J. and Broad, A. "Pilocarpine delivery by hydrophilic lens in the management of acute glaucoma" Trans. Ophthal. Soc.U. K. (1975)p. 79-84.

Giambattista, B.,Virno, M., Pecori-Giraldi, Pellegrino, N. and Motolese, E. "Possibility of Isoproterenol Therapy with Soft Contact Lenses: Ocular Hypotension Without Systemic Effects" Ann. Ophthalmol 8 (1976) p. 819-829.

Marmion, V. J. and Yardakul, S. "Pilocarpine administration by contact lens" Trans. Ophthal. Soc.U. K. 97, (1977) p. 162-3.

Elisseeff, J., McIntosh, W., Anseth, K., Riley, S., Ragan, P., Langer, R., "*Photoencapsulation of chondrocytes in poly(ethylene oxide)-based semi-interpenetrating networks*", Journal of Biomedical Materials Research, 2000, 51 (2): 164-171.

Ward, J. H., Peppas, N. A., "*Preparation of controlled release systems by free-radical UV polymerizations in the presence of a drug*", Journal of Controlled Release, 2001, 71 (2): 183-192.

Scott, R. A., Peppas, N. A., "*Highly crosslinked, PEG-containing copolymers for sustained solute delivery*", Biomaterials, 1999, 20 (15): 1371-1380.

Podual, K., Doyle F. J., Peppas N. A., "*Preparation and dynamic response of cationic copolymer hydrogels containing glucose oxidase*", Polymer, 2000, 41 (11): 3975-3983.

Colombo, P., Bettini, R., Peppas, N.A., "*Observation of swelling process and diffusion front position during swelling in hydroxypropyl methyl cellulose (HPMC) matrices containing a soluble drug*", Journal of Controlled Release, 1999, 61 (1,2): 83-91.

Ende, M.T.A., Peppas, N.A., "*Transport of ionizable drugs and proteins in crosslinked poly(acrylic acid) and poly(acrylic acid-co-2-hydroxyethyl methacrylate) hydrogels. 2. Diffusion and release studies*", Journal of Controlled Release, 1997, 48 (1): 47-56.

Hiratani H, Alvarez-Lorenzo C—"The nature of backbone monomers determines the performance of imprinted soft contact lenses as timolol drug delivery systems" Biomaterials 25,1105-1113, 2004.

Hiratani H, Fujiwara A, Tamiya Y, Mizutani Y, Alvarez-Lorenzo C—"Ocular release of timolol from molecularly imprinted soft contact lenses" Biomaterials 26,1293-1298, 2005.

Hiratani H, Mizutani Y, Alvarez-Lorenzo C—"Controlling drug release from imprinted hydrogels by modifying the characteristics of the imprinted cavities" Macromol Biosci 5,728-733, 2005.

Alverez-Lorenzo C, Hiratani H, Gomez-Amoza JL, Martinez-Pacheco R, Souto C, Concheiro A—"Soft contact lenses capable of sustained delivery of timolol" J Pharm Sci 91,2182-2192, 2002.

Hiratani H, Alvarez-Lorenzo C—"Timolol uptake and release by imprinted soft contact lenses made of N,N-diethylacrylamide and methacrylic acid" J Control Release 83,223-230, 2002.

Gulsen, Derya, "Ophthalmic drug delivery system", Gulsen D, Chauhan A—"Dispersion of microemulsion drops in HEMA hydrogel: a potential ophthalmic drug delivery vehicle". Int J Pharm 292,95-117, 2005.

Gulsen D, Chauhan A—"Ophthalmic drug delivery through contact lenses". Invest Ophth Vis Sci 45,2342-2347, 2004.

Graziacascone, M., Zhu, Z., Borselli, F., Lazzeri, L., "Poly(vinyl alcohol) hydrogels as hydrophilic matrices for the release of lipophilic drugs loaded in PLGA nanoparticles", Journal of Material Science: Materials in Medicine, 2002, 13: 29-32.

Mandell, R.B., "*Contact Lens Practice: Hard and Flexible Lenses*", 2nd ed., Charles C. Thomas, Springfield, vol. 3, 1974].

Creech, J.L., Chauhan, A., Radke, C.J., "*Dispersive mixing in the posterior tear film under a soft contact lens*", I&EC Research, 2001, 40: 3015-3026.

McNamara, N.A., Polse, K.A., Brand, R.D., Graham, A.D., Chan, J.S., McKenney, C.D., "*Tear mixing under a soft contact lens: Effects of lens diameter*". Am. J. of Ophth., 1999, 127(6): 659-65.

Letter from Korean Associate dated May 10, 2008, informing of Office Action issued on Apr. 27, 2008 for corresponding Korean Patent Application No. 2004-7019648 based on International application No. PCT/US03/17736 for "Ophthalmic Drug Delivery System".

\* cited by examiner

US 8,071,121 B2

DISPERSIONS OF MICROEMULSIONS IN HYDROGELS FOR DRUG DELIVERY

CROSS-REFERENCE TO RELATED APPLICATIONS:

This application is a Continuation-in-Part of application Ser. No. 10/802,058, filed Mar. 17, 2004, which is a Continuation-in-Part of application Ser. No. 10/454,836 filed Jun. 5, 2003, now U.S. Pat. No. 7,638,137 which claims priority to Provisional Application No. 60/385,571 filed Jun. 5, 2002, the entire contents of each being hereby incorporated by reference in their respective entirety.

BACKGROUND OF THE INVENTION

1. Field of the Invention

The present invention relates to methods and systems for the delivery of drugs to patients in need thereof.

2. Description of the Prior Art

Providing and maintaining adequate concentrations of bioactive agents, such as drugs, for example, in the pre-corneal tear film for extended periods of time is one of the major problems plaguing methods and systems for ocular drug delivery. When they are applied as eye drops, most drugs penetrate poorly through the cornea. Drainage of instilled drug with the tear fluid, and absorption through the conjunctiva leads to a short duration of action. The additional pre-corneal factors that contribute to the poor ocular bio-availability of many drugs when instilled in the eye as drops are tear turnover and drug binding to tear fluid proteins. In addition to the above factors, the rate of corneal uptake is high at early times, but it declines rapidly. This may lead to a transient period of overdose and associated risk of side effects followed by an extended period of sub-therapeutic levels before the administration of next dose. All the above factors indicate the need for an ocular drug delivery system that will be as convenient as a drop but will serve as a controlled release vehicle [Nagarsenker, M. S., Londhe, V. Y., Nadkarni, G. D., "*Preparation and evaluation of liposomal formulations of tropicamide for ocular delivery*", Int. J. of Pharm., 1990, 190: 63-71].

Topical delivery via eye drops that accounts for about 90% of all ophthalmic formulations is very inefficient and in some instances leads to serious side effects [Lang, J. C., "*Ocular drug delivery conventional ocular formulations*". Adv. Drug Delivery, 1995, 16: 39-43]. Only about 5% of the drug applied as drops penetrate through the cornea and reaches the ocular tissue, while the rest is lost due to tear drainage. [Bourlais, C. L., Acar, L., Zia H., Sado, P. A., Needham, T., Leverge, R., "*Ophthalmic drug delivery systems*", Progress in retinal and eye research, 1998, 17, 1: 33-58]. The drug mixes with the fluid present in the tear film upon instillation and has a short residence time of about 2-5 minutes in the film. About 5% of the drug gets absorbed and the remaining flows through the upper and the lower canaliculi into the lacrimal sac. The drug containing tear fluid is carried from the lacrimal sac into the nasolacrimal duct, and eventually, the drug gets absorbed into the bloodstream. This absorption leads to drug wastage and more importantly, the presence of certain drugs in the bloodstream may lead to undesirable side effects. For example, beta-blockers such as Timolol that is used in the treatment of wide-angle glaucoma may have a deleterious effect on heart [TIMPOTIC® prescribing information, supplied by MERCK]. Furthermore, application of ophthalmic drugs as drops may result in a rapid variation in drug delivery rates to the cornea that limits the efficacy of therapeutic systems [Segal, M., "*Patches, pumps and timed release*", FDA Consumer magazine, October 1991]. Thus, there is a need for new ophthalmic drug delivery systems that increase the residence time of the drug in the eye, thereby reducing wastage and minimizing or eliminating side effects.

There have been a number of attempts in the past to use contact lenses for ophthalmic drug delivery; however, all of these focused on soaking the lens in drug solution followed by insertion into the eye. In one of the studies, the authors focused on soaking the lens in eye-drop solutions for one hour followed by lens insertion in the eye [Hehl, E. M., Beck, R., Luthard K., Guthoff R., "*Improved penetration of aminoglycosides and fluoroquinolones into the aqueous humour of patients by means of Acuvue contact lenses*", European Journal of Clinical Pharmacology, 1999, 55 (4): 317-323]. Five different drugs were studied and it was concluded that the amount of drug released by the lenses are lower or of the same order of magnitude as the drug released by eye drops. This happened perhaps because the maximum drug concentration obtained in the lens matrix is limited to the equilibrium concentration. In another study researchers developed a contact lens with a hollow cavity by bonding together two separate pieces of lens material [Nakada, K., Sugiyama, A., "*Process for producing controlled drug-release contact lens, and controlled drug-release contact lens thereby produced*"; U.S. Pat. No. 6,027,745, May 29, 1998]. The compound lens is soaked in the drug solution. The lens imbibes the drug solution and slowly releases it upon insertion in the eye. The compound lens suffers from the same limitations as the drug-soaked lens because the concentration of the drug in the cavity is the same as the concentration of the drug in the drops and thus such a lens can supply the drug for a limited amount of time.

Furthermore, the presence of two separate sheets of lens material leads to smaller oxygen and carbon dioxide permeabilities that can cause an edema in the corneal tissue. The other studies and patents listed below suffer from the same limitations because they are also based on soaking of contact lenses or similar devices in drug-solutions followed by insertion into the eye [Hillman, J. S., "Management of acute glaucoma with Pilocarpine-soaked hydrophilic lens" Brit. J. Ophthal. 58 (1974) p. 674-679, Ramer, R. and Gasset, A., "Ocular Penetration of Pilocarpine:" Ann. Opthalmol. 6, (1974) p. 1325-1327, Montague, R. and Wakins, R., "Pilocarpine dispensation for the soft hydrophilic contact lens" Brit. J. Ophthal. 59, (1975) p. 455-458, Hillman, J., Masters, J. and Broad, A. "Pilocarpine delivery by hydrophilic lens in the management of acute glaucoma" Trans. Ophthal. Soc. U. K. (1975) p. 79-84, Giambattista, B., Virno, M., Pecori-Giraldi, Pellegrino, N. and Motolese, E. "Possibility of Isoproterenol Therapy with Soft Contact Lenses: Ocular Hypotension Without Systemic Effects" Ann. Opthalmol 8 (1976) p. 819-829, Marmion, V. J. and Yardakul, S. "Pilocarpine administration by contact lens" Trans. Ophthal. Soc. U. K. 97, (1977) p. 162-3, U.S. Pat. No. 6,410,045, Drug delivery system for antiglaucomatous medication, Schultz; Clyde Lewis, Mint; Janet M; U.S. Pat. No. 4,484,922, Occular device, Rosenwald; Peter L., U.S. Pat. No. 5,723,131, Contact lens containing a leachable absorbed material, Schultz; Clyde L. Nunez; Ivan M.; Silor; David L.; Neil; Michele L.].

A number of researchers have trapped proteins, cells and drugs in hydrogel matrices by polymerizing the monomers that comprise the hydrogel, in presence of the encapsulated species [Elisseeff, J., McIntosh, W., Anseth, K., Riley, S., Ragan, P., Langer, R., "*Photoencapsulation of chondrocytes in poly(ethylene oxide)-based semi-interpenetrating networks*", Journal of Biomedical Materials Research, 2000, 51

(2): 164-171; Ward, J. H., Peppas, N. A., "*Preparation of controlled release systems by free-radical UV polymerizations in the presence of a drug*", Journal of Controlled Release, 2001, 71 (2): 183-192; Scott, R. A., Peppas, N. A., "*Highly crosslinked, PEG-containing copolymers for sustained solute delivery*", Biomaterials, 1999, 20 (15): 1371-1380; Podual, K., Doyle F. J., Peppas N. A., "*Preparation and dynamic response of cationic copolymer hydrogels containing glucose oxidase*", Polymer, 2000, 41 (11): 3975-3983; Colombo, P., Bettini, R., Peppas, N. A., "*Observation of swelling process and diffusion front position during swelling in hydroxypropyl methyl cellulose (HPMC) matrices containing a soluble drug*", Journal of Controlled Release, 1999, 61 (1,2): 83-91; Ende, M. T. A., Peppas, N. A., "*Transport of ionizable drags and proteins in crosslinked poly(acrylic acid) and poly(acrylic acid-co-2-hydroxyethyl methacrylate) hydrogels. 2. Diffusion and release studies*", Journal of Controlled Release, 1997, 48 (1): 47-56; U.S. Pat. No. 4,668,506]. Direct entrapment of drug could increase loading but it does not increase the duration of release.

A number of researchers have focused on developing 'imprinted' contact lenses [Hiratani H, Alvarez-Lorenzo C—"The nature of backbone monomers determines the performance of imprinted soft contact lenses as timolol drug delivery systems" Biomaterials 25, 1105-1113, 2004; Hiratani H, Fujiwara A, Tamiya Y, Mizutani Y, Alvarez-Lorenzo C—"Ocular release of timolol from molecularly imprinted soft contact lenses" Biomaterials 26, 1293-1298, 2005; Hiratani H, Mizutani Y, Alvarez-Lorenzo C-"Controlling drug release from imprinted hydrogels by modifying the characteristics of the imprinted cavities" Macromol Biosci 5,728-733, 2005: Alverez-Lorenzo C, Hiratani H, Gomez-Amoza J L, Martinez-Pacheco R, Souto C, Concheiro A—"Soft contact lenses capable of sustained delivery of timolol" J Pharm Sci 91, 2182-2192, 2002; Hiratani H, Alvarez-Lorenzo C—"Timolol uptake and release by imprinted soft contact lenses made of N,N-diethylacrylamide and methacrylic acid" J Control Release 83,223-230, 2002]. These articles disclose that imprinting leads to an increase in the partition coefficients and slower release of drugs, but the increase is not very substantial, and these lenses typically have an initial burst release.

To substantially increase the duration of drug release, Chauhan et al suggested dispersing in contact lenses nanoparticles of ophthalmic bioactive agents nanoencapsulated in a material from which the ophthalmic drug is capable of diffusion into and migration through the contact lens and into the post-lens tear film when the contact lens is placed on the eye. The particle size of the nanoparticles and the number thereof dispersed in the contact lens are such that the contact lens remains substantially transparent. [United States Published Patent Applications 20040241207 and 20040096477], Chauhan, Anuj; http://appft1.uspto.gov/netacgi/nph-Parser?Sect1=PTO2&Sect2=HITOFF&p=1&u=%2Fnetahtml%2FPTO%2Fsearch-bool.html&r=2&f=G&l=50&col=AND&d=PG01&s1=gulsen&s2=chauhan&OS=gulsen+AND+chauhan&RS=gulsen+AND+chauhan-h2http://appft1.uspto.gov/netacgi/nph-Parser?Sect1=PTO2&Sect2=HITOFF&p=1&u=%2Fnetahtml%2FPTO%2Fsearch-bool.html&r=2&f=G&l=50&col=AND&d=PG01&s1=gulsen&s2=chauhan&OS=gulsen+AND+chauhan&RS=gulsen+AND+chauhan-h4Gulsen, Derya, "Ophthalmic drug delivery system", Gulsen D, Chauhan A—"Dispersion of microemulsion drops in HEMA hydrogel: a potential ophthalmic drug delivery vehicle". Int J Pharm 292, 95-117, 2005., Gulsen D, Chauhan A—"Ophthalmic drug delivery through contact lenses". Invest Ophth Vis Sci 45, 2342-2347, 2004]. Also Graziacascone et al. discloses a study on encapsulating lipophilic drugs inside nanoparticles, and entrapping the particles in hydrogels. [Graziacascone, M., Zhu, Z., Borselli, F., Lazzeri, L., "Poly(vinyl alcohol) hydrogels as hydrophilic matrices for the release of lipophilic drugs loaded in PLGA nanoparticles", Journal of Material Science: Materials in Medicine, 2002, 13: 29-32]. They used PVA hydrogels as hydrophilic matrices for the release of lipophilic drugs loaded in PLGA particles. There are two main advantages of entrapment of drug in nanoparticles over soaking and direct entrapment of drug in a gel. First, if the solute is directly trapped in the gel, the release rates are controlled by diffusion through the gel. Contact lenses must be very thin (about 100 µm thick) and only lightly crosslinked to ensure high oxygen permeability. Thus, if drugs are directly trapped in the lens during polymerization, they will be released in a short period of time. If the drugs are trapped inside the nanoparticles, and if the nanoparticles are designed to release drugs slowly, then a contact lens loaded with the drug containing particles can release drug for longer periods of time. Secondly, since the solubility of the hydrophobic drugs is much higher in oil, a significantly higher drug loading can be achieved by entrapping the drug in oil filled nanoparticles or nanocapsules, and subsequently, dispersing these particles in a hydrogel matrix.

In a copending patent application there is disclosed a bioactive agent delivery system comprising a substantially optically transparent contact lens having dispersed therein (1) an ophthalmically bioactive agent, the agent being capable of diffusion through the contact lens and into the post-lens tear film when the contact lens is placed on the eye and (2) associated with the bioactive agent, at least one ophthalmically compatible surfactant, the polymeric surfactant being present in an amount sufficient to attenuate the rate of migration of the bioactive agent through the contact lens.

It is an object of the present invention to provide a novel bioactive agent delivery system, particularly adapted for delivering the agent to the eye.

SUMMARY OF THE INVENTION

The above and other objects are achieved by the present invention, one embodiment of which relates to an ophthalmically bioactive agent delivery system comprising a contact lens having dispersed therein as an oil-in-water microemulsion, an ophthalmically bioactive agent encapsulated in the oil phase of the microemulsion, the oil phase comprising an ophthalmically acceptable material from which the agent is capable of diffusion into and migration through the contact lens and into the post-lens tear film when the contact lens is placed on the eye and wherein the microemulsion is stabilized by the presence of an ophthalmically acceptable surfactant with sufficient packing at the oil-water interface to attenuate the rate of diffusion into and migration of agent through the contact lens.

A second embodiment of the invention is a method of administering a bioactive agent to a patient in need thereof comprising placing on the eye the above described drug delivery system.

Third and fourth embodiments of the invention concern a kit and its use for the storage and delivery of ophthalmic drugs to the eye, the kit comprising:

a) a first component containing at least one of the above described drug delivery systems, and b) a second component containing at least one storage container for the first component, the storage container additionally containing a material that substantially prevents the fusion and migration of the ophthalmic drug during storage.

A fifth embodiment of the invention relates to a method of manufacturing a bioactive agent delivery system of claim 1 comprising providing a reactive mixture comprising at least one lens-forming component, the surfactant and the bioactive agent and polymerizing said monomer mixture.

Sixth and seventh embodiments of the invention concern articles of manufacture comprising packaging material and the above described drug delivery system or the above-described kit contained within the packaging material, wherein the packaging material comprises a label which indicates that the drug delivery system and kit can be used for ameliorating symptoms associated with pathologic conditions of the eye.

DETAILED DESCRIPTION OF THE INVENTION

Figure 1:
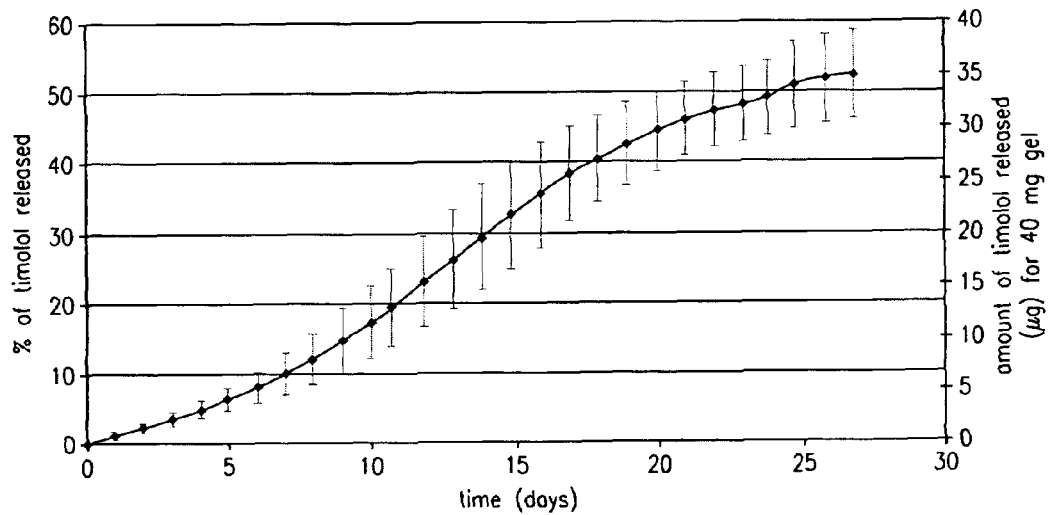
FIGS. 1-6 are graphical plots of drug release profiles for several embodiments of the invention.

The contact lenses of the present invention are formed from reaction mixtures which comprise the reactive components, catalyst, other desired components, and optionally a solvent. The reaction mixtures may be cured using conventionally known conditions, which need not be described here.

Hydrophilic components are those which when mixed, at 25° C. in a 1:1 ratio by volume with neutral, buffered water (pH about 7.0) forms a homogenous solution. Any of the hydrophilic monomers known to be useful to make hydrogels may be used.

In one embodiment the hydrophilic monomer comprises at least one of DMA, HEMA, glycerol methacrylate, 2-hydroxyethyl methacrylamide, NVP, N-vinyl-N-methyl acrylamide, N-methyl-N-vinylacetamide, polyethyleneglycol monomethacrylate, methacrylic acid and acrylic acid, polymers and copolymers of any of the foregoing, combinations thereof and the like.

The reaction mixtures may also comprise at least one hydrophobic component. Hydrophobic components are those which when mixed, at 25° C. in a 1:1 ratio by volume with neutral, buffered water (pH about 7.0) form an immiscible mixture.

Examples of suitable hydrophobic components include silicone containing components, fluorine containing components, components comprising aliphatic hydrocarbon groups having at least 3 carbons, combinations thereof and the like.

The term component includes monomers, macromers and prepolymers. "Monomer" refers to lower molecular weight compounds that can be polymerized to higher molecular weight compounds, polymers, macromers, or prepolymers. The term "macromer" as used herein refers to a high molecular weight polymerizable compound. Prepolymers are partially polymerized monomers or monomers which are capable of further polymerization.

The present invention is predicated on the discovery that contact lenses, preferably, soft contact lenses can function as new vehicles for ophthalmic drug delivery to reduce drug loss, eliminate systemic side effects, and improve drug efficacy.

The crux of the invention resides in the discovery that the rate of migration of bioactive agents, capable of diffusion through contact lenses and into the post-lens tear film when the contact lens is placed on the eye, is attenuated where the bioactive agent is an oil-in-water microemulsion and the ophthalmically bioactive agent is encapsulated in the oil phase of the microemulsion and the microemulsion is stabilized by the presence of a surfactant with sufficient packing at the oil-water interface The invention is exemplified herein using soft hydrogel lenses that comprise poly 2-hydroxyethyl methacrylate p-(HEMA). However, it will be understood by those skilled in the art that the range of materials that may be employed as vehicles in the present invention is limited only by the selection of materials that may be employed in the manufacture of contact lenses and the nature of the particular ophthalmic drug to be incorporated therein. The term, "optically transparent" as used herein is intended to refer to a degree of transparency equivalent to that of p-HEMA or other material employed as a contact lens. The p-HEMA hydrogel matrix may be synthesized by any convenient method, e.g., bulk or solution free radical polymerization of HEMA monomers in presence of a cross linker such as ethylene glycol-dimethacrylate (EGDMA) [Mandell, R. B., "*Contact Lens Practice: Hard and Flexible Lenses*", $2^{nd}$ ed., Charles C. Thomas, Springfield, vol. 3, 1974].

Addition of the bioactive agent to the reaction mixture results in the formation of a microemulsion of the bioactive agent in the hydrogel matrix upon polymerization. If contact lenses made of this material are placed on the eye, the drug molecules will diffuse from the particles, travel through the lens matrix, and enter the post-lens tear film (POLTF), i.e., the thin tear film trapped in between the cornea and the lens. In the presence of the lens, drug molecules will have a much longer residence time in the post-lens tear film, compared to about 2-5 minutes in the case of topical application as drops [Bourlais, C. L., Acar, L., Zia H., Sado, P. A., Needham, T., Leverge, R., "*Ophthalmic drug delivery systems*", Progress in retinal and eye research, 1998, 17, 1: 33-58; Creech, J. L., Chauhan, A., Radke, C. J., "*Dispersive mixing in the posterior tear film under a soft contact lens*", I&EC Research, 2001, 40: 3015-3026; McNamara, N. A., Poise, K. A., Brand, R. D., Graham, A. D., Chan, J. S., McKenney, C. D., "*Tear mixing under a soft contact lens: Effects of lens diameter*". Am. J. of Ophth., 1999, 127(6): 659-65]. The longer residence time will result in a higher drug flux through the cornea and reduce the drug inflow into the nasolacrimal sac, thus reducing drug absorption into the blood stream. In addition, due to the slow diffusion of the drug molecules through the particles, drug-laden contact lenses can provide continuous drug release for extended periods of time.

Without wishing to be bound by any theory, the inventors believe that the mechanism of attenuation of migration of the active agent is a slowing of migration of the active agent from the oil-in-water emulsion by the packing of the surfactant at the oil-water interface. An alternate possibility is that the surfactants present in the microemulsion form other types of structures inside the gel such as micelles, and these structures lead to a slow down in the release rates.

Suitable surfactants include any ophthalmically compatible surfactants capable of sufficient packing at the oil-water interface to attenuate migration therefrom of the active agent, but which does not deleteriously affect the optical transparency of the resulting contact lens. Exemplary of suitable surfactants are the Brij compounds; i.e., linear ethoxylated surfactant containing the same alkyl chain length (CIS) and increasing numbers of ethoxylate (EO) units (e.g., 10, 20, and 100).

Exemplary of bioactive agents that may be delivered according to the present invention are timolol and cyclosporine; although it will be understood that the selection of any suitable bioactive agent for delivery to the eye is well within the skill of the art. In the examples, the following materials were employed: HEMA monomer and ethylene glycol dimethacrylate (EGDMA); ethyl butyrate and benzoyl peroxide; timolol maleate, pluonic F127, Dulbecco's phosphate buffered saline (PBS), sodium caprylate, and sodium hydroxide pellets (99.998%); Darocur TPO and cyclosporine.

EXAMPLES

Example 1

The first step in synthesis of gels loaded with drug containing microemulsions requires synthesis of an oil-in-water microemulsion. Hydrophobic drugs such as cyclosporine, dexamethasone, or even the base form of timolol can be dissolved in the oil phase of the microemulsion. The microemulsions are then added to HEMA monomer and polymerized to form a HEMA gel laden with drug containing microemulsion drops.

Synthesis of Pluronic microemulsions: The microemulsions described below utilize ethyl butyrate as the oil phase, Pluronic F 127 as the surfactant, and sodium caprylate as the co-surfactant. In these studies, the base form of timolol is entrapped in the oil drops of the microemulsions. The fraction of drug in the oil phase and also the fraction of the oil phase in the microemulsions are varied to develop systems with different drug loadings. Four types of microemulsions are described below. They are referred to as meA, meB, meC, and meD.

To make meA, first dissolve 0.0831 g of timolol maleate salt in 6 ml of 0.77M NaOH solution. The pH of the resulting solution is above the pKa of timolol (pKa-9.2), and thus the base form of timolol separated out from the aqueous solution. After allowing the mixture to phase separate, pipette out 5 ml of the aqueous phase, and added 400 µl of ethyl butyrate to extract the timolol base. After extraction, separate the upper oil phase (timolol base dissolved in ethyl butyrate) and the lower aqueous phase. The upper phase (timolol containing ethyl butyrate which is referred as T/E below) was used as the oil phase of the microemulsions MeA is water-in-oil (W/O) microemulsion stabilized by Pluronic F127 surfactant and sodium caprylate co-surfactant. To make the surfactant solution, dissolve 1.2 g of Pluronic F127 and 0.0163 g of sodium caprylate in 9 ml saline (0.85 wt % NaCl in DI water). In order to dissolve the surfactant in the aqueous solution, the mixture had to be stirred at about 600 rpm at room temperature for a period of about 5 hours. Add 0.1 ml T/E and 0.5 ml of 1.5M NaOH solution to 4.5 ml of the surfactant solution, and stirred the mixture at 600 rpm at room temperature. After about 3 hours, the solution turned clear, which indicated microemulsion formation.

MeB was made by the same procedures as meA, except that meB has a slightly higher content of oil phase than meA. To synthesize meB, 0.15 ml instead of 0.1 ml TIE was added to 4.5 ml of surfactant solution.

MeC was also made by similar procedures as meA. For preparing meC, pure timolol base was used as the oil phase instead of a mixture of timolol and ethyl butyrate. To synthesize meC, 0.1642 g of timolol maleate was added to 6 ml of 1.5 M NaOH solution to generate timolol base, and the mixture was allowed to phase separate. Then pipette out and discard 5 ml of the top aqueous phase, and the rest of the mixture was dried by blowing nitrogen for about 30 minutes. Separately dissolve 2.145 g of Pluronic F127 and 0.016 g of sodium caprylate in 8 ml saline (0.85 wt % NaCl in DI water) for use as the surfactant solution for meC. In order to dissolve the surfactant in the aqueous solution, the mixture had to be stirred at about 600 rpm at room temperature for a period of about 5 hours. Then add 1 ml of 2.31 M NaOH solution, 4 ml surfactant solution, and 0.383 g more Pluronic F127 to the "dried" timolol base, and stir the mixture at 600 rpm at room temperature for 3 hours.

MeD was also made by similar procedures as meA, except that it had a slightly higher content of timolol in T/E mixture, a slightly higher oil content in the microemulsion, as well as a higher total amount of surfactant added to the microemulsion. Specifically, 0.1222 g of timolol maleate was added to 6 ml of 0.77 M NaOH solution to generate timolol base, and the mixture was allowed to phase separate. Then pipette out and discard 5 ml of the top aqueous phase, and extracted timolol base with 230 µl ethyl butyrate. Separately dissolve 1.64 g of Pluronic F127 in 9 ml saline (0.85 wt % NaCl in DI water) as the surfactant solution for meD. In order to dissolve the surfactant in the aqueous solution, the mixture had to be stirred at about 600 rpm at room temperature for a period of about 5 hours. Then add 0.1 ml TIE and 0.5 ml of 1.5 M NaOH solution to 4.5 ml of the surfactant solution, and stir the above solution at 600 rpm at room temperature for 3 hours.

The compositions of the four types of microemusions described above are summarized in Table 1.

TABLE 1

Compositions of various Pluronic microemulsions (me) 1.2

| ID | Oil % in me | Surf % in me | Drug % in oil | Drug % in me |
|----|-------------|--------------|---------------|--------------|
| A  | 1.73        | 10.4         | 14.76         | 0.254        |
| B  | 2.48        | 10.3         | 14.6          | 0.362        |
| C  | 2.18        | 15.5         | 100           | 2.18         |
| D  | 1.96        | 13.4         | 30            | 0.58         |

Example 2

Entrapment of Pluronic Microemulsions in HEMA Gels

The microemulsion-loaded p-HEMA hydrogels were synthesized by free radical solution polymerization with UV initiation. 1.35 ml of the monomer hydroxylethyl methacrylate (HEMA), 5 µl of ethylene glycol dimethacrylate (EGDMA), and 1 ml of the microemulsion were mixed together in a glass tube. This solution was degassed by bubbling nitrogen for 15 minutes to reduce the amount of dissolved oxygen which can be a scavenger of both initiating and propagating species in free radical polymerization. Next, 3 mg of the photoinitiator, Darocur TPO, was added to the mixture, and the solution was stirred for 10 minutes. The resulting mixture was poured in between two glass plates separated by a 200 µm plastic spacer. The mold was then put on a UVB-light illuminator for 40 minutes for gel curing. Pure p-HEMA gels were synthesized by replacing the microemulsion by an equal volume of DI water.

Example 3

Timolol Release in DI Water with Water Replacement every 24 Hours

After polymerization, each gel was removed from the glass mold, and was cut into pieces that were above about 1.5 cm in length and width and about 200 μm in thickness. Each piece of gel was dried in the air overnight and then weighed the next day. The gel was then submerged in 200 ml deionized (DI) water bath under minimal stirring and at room temperature for 5 hours to extract the unreacted monomer. This step is referred to as the extraction or the initial soaking step. The fraction of drug that diffused out during the extraction step was determined by measuring the absorbance at wavelengths near the absorbance peak of timolol (295 nm). The fractions of drug released in the extraction step for various types of gels are listed in the Table 2 below.

TABLE 2

Fractional drug release in the extraction step for various types of microemulsion-laden gels.

| gel type | gel weight g | initial timolol input mg | released during initial soaking mg | % |
|---|---|---|---|---|
| A | 0.060 | 0.095 | 0.016 | 17.5 |
| B | 0.064 | 0.144 | 0.018 | 12.55 |
| C | 0.072 | 0.848 | 0.064 | 7.56 |
| D | 0.049 | 0.179 | 0.023 | 12.67 |

Figure 2:
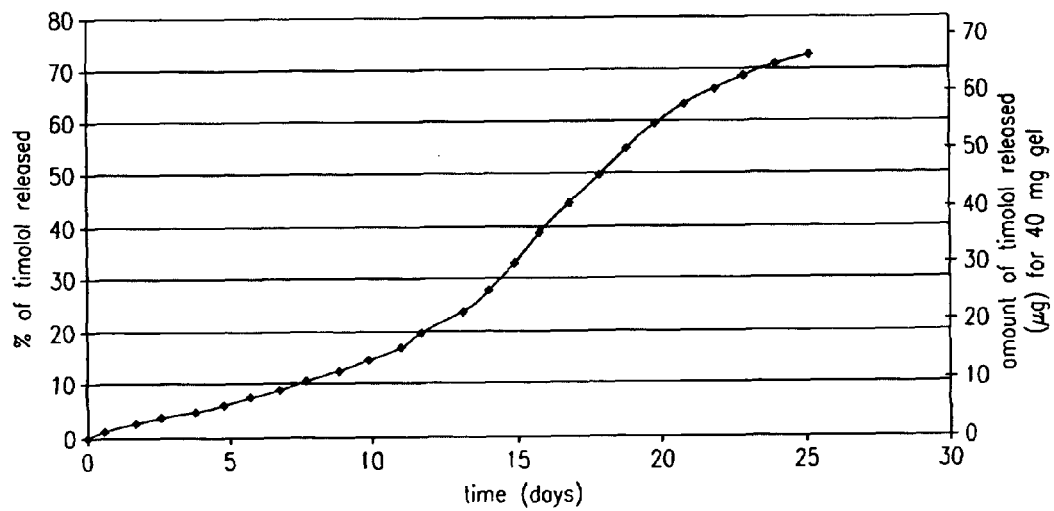
Figure 3:
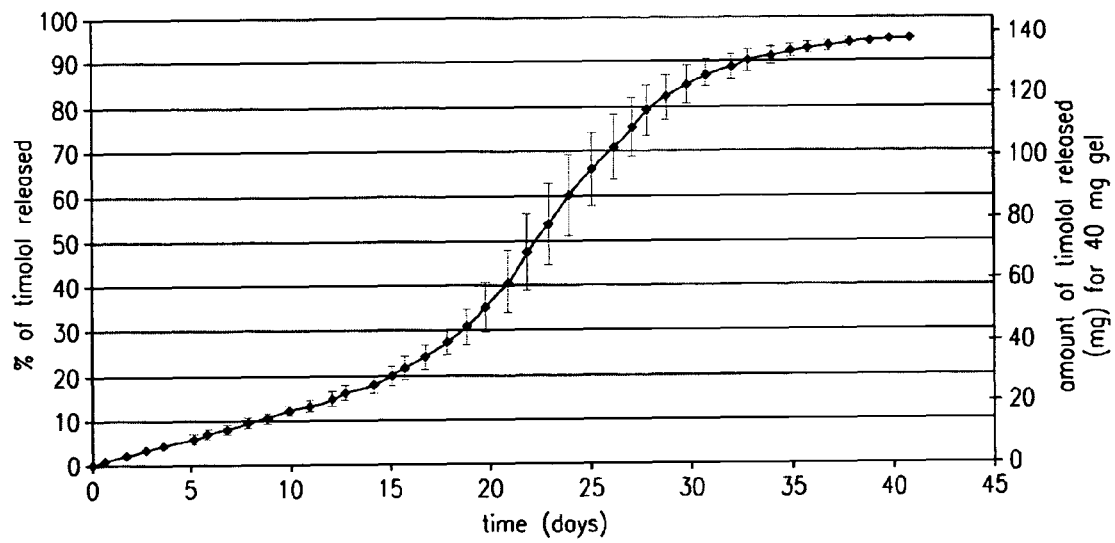
Figure 4:
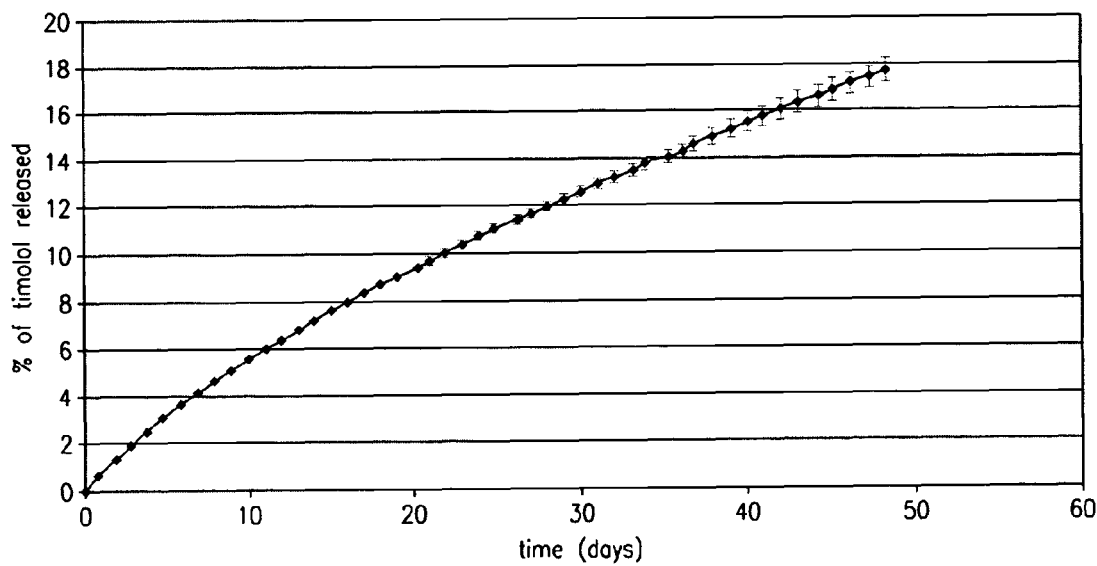

After the extraction step, the gels were transferred into 3 ml of DI water for the drug release experiments. The DI water was replaced every day, and the absorbance of the sample was measured at the instance of water replacement. FIGS. 1-4 plot the drug release profiles for gels A-D [FIG. 1: Timolol release in DI water for meA laden PHEMA gels. The errors bars denote standard deviation, n=4; FIG. 2: Timolol release in DI water for a meB laden PHEMA gel; FIG. 3: Timolol release in DI water for meD laden PHEMA gels. The errors bars denote standard deviation, n=2 and FIG. 4: Timolol release in DI water for meC laden PHEMA gels. The errors bars denote standard deviation, n=2].

In these plots the cumulative release of timolol is plotted as a percentage of the total amount of drug that was initially loaded into the gels. The results show that each of the gel releases drug for about 25 days. The release curves show a sigmoidal behavior. On adding the drug percentages that were released during the extraction step to the percentage release plotted in FIGS. 1-4, one obtains about 100% release for gels except for gel A, in which case the total amount of drug released is only about 78% of the loaded drug. The release experiments for gel C (gel loaded with pure timolol microemulsion) were stopped after about 50 days during which only about 20% of the drug diffused out. The similarities in drug release profiles in FIGS. 1-3 show that the microstructure of all of the gels are relatively similar, and that the drug release rate is linear in drug concentration. The release profiles are encouraging because the gels continue to release the drug for a period of about 25 days. However, it must be noted that these release experiments were performed in DI water, which may not be a good mimic of the tear environment particularly for ionizable drugs such as timolol.

Example 4

Figure 5:
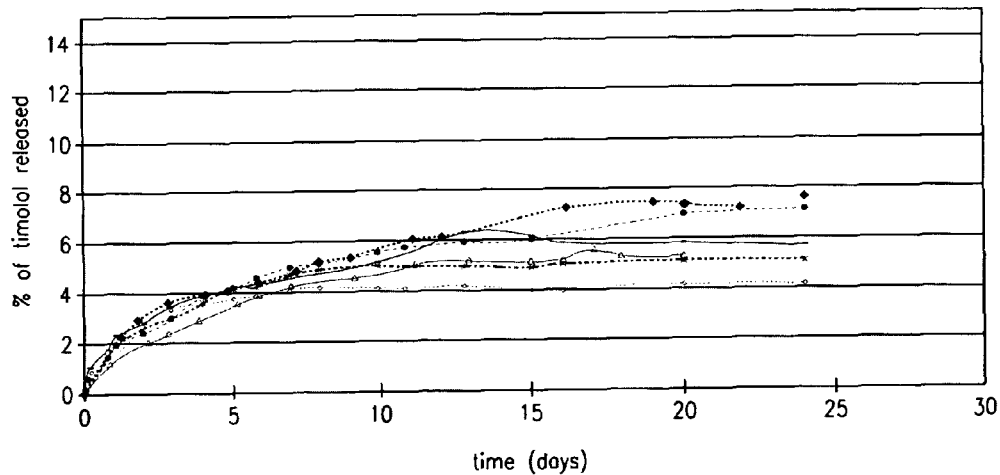

Timolol Release from Pluronic Microemulsion-Laden Gels in DI Water without Water Replacement These experiments were performed to determine the equilibrium release time for the microemulsion-laden gels. The protocols for these experiments were identical to those described above, except that the gel was kept in the same 3 ml DI water during the entire course of the drug release experiments. These equilibrium experiments were only done on gel A. These gels lost 17.5% of the entrapped drug during the extraction phase. The results of drug release experiments FIG. 5 (Timolol released in DI water without water replacement for meA laden PHEMA gels (n=6) show that about 8% of the entrapped drug diffuses out in a period of about 10 days.

Example 5

Timolol Release from Pluronic Microemulsion-Laden Gels in PBS

Figure 6:
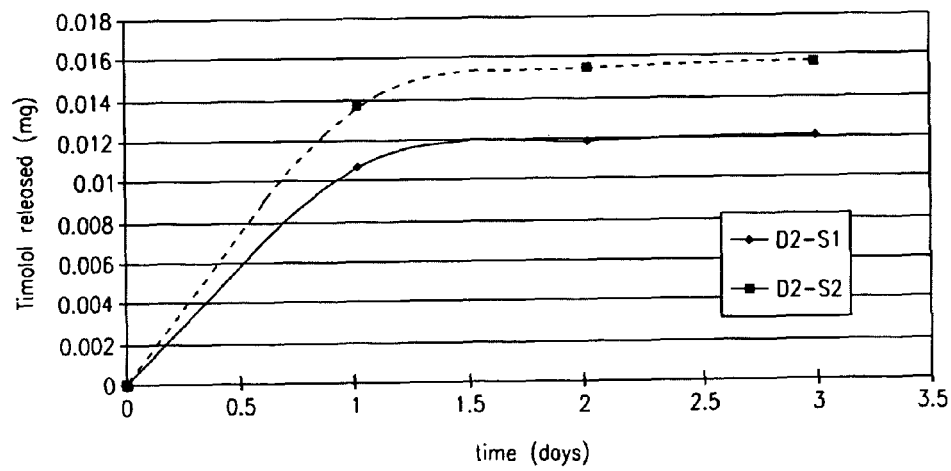

Protocols identical to those described above were followed, except that the DI water was replaced by PBS or saline both in the extraction and the drug release steps. The release in saline and PBS was much more rapid compared to the release in DI water. The extraction phase for these studies was conducted in 10 ml of saline. In both PBS and saline, about 90% of the drug diffused out during the extraction phase, and the remaining amount is released in the first 1.5 hours of the drug release experiments. See FIG. 6 (Drug release in saline for gel D. The numbers on the curves indicate the fractional release during extraction).

Example 6

Synthesis of Pluronic Microemulsions with HEMA-water as the Continuous Phase

Figure 7:
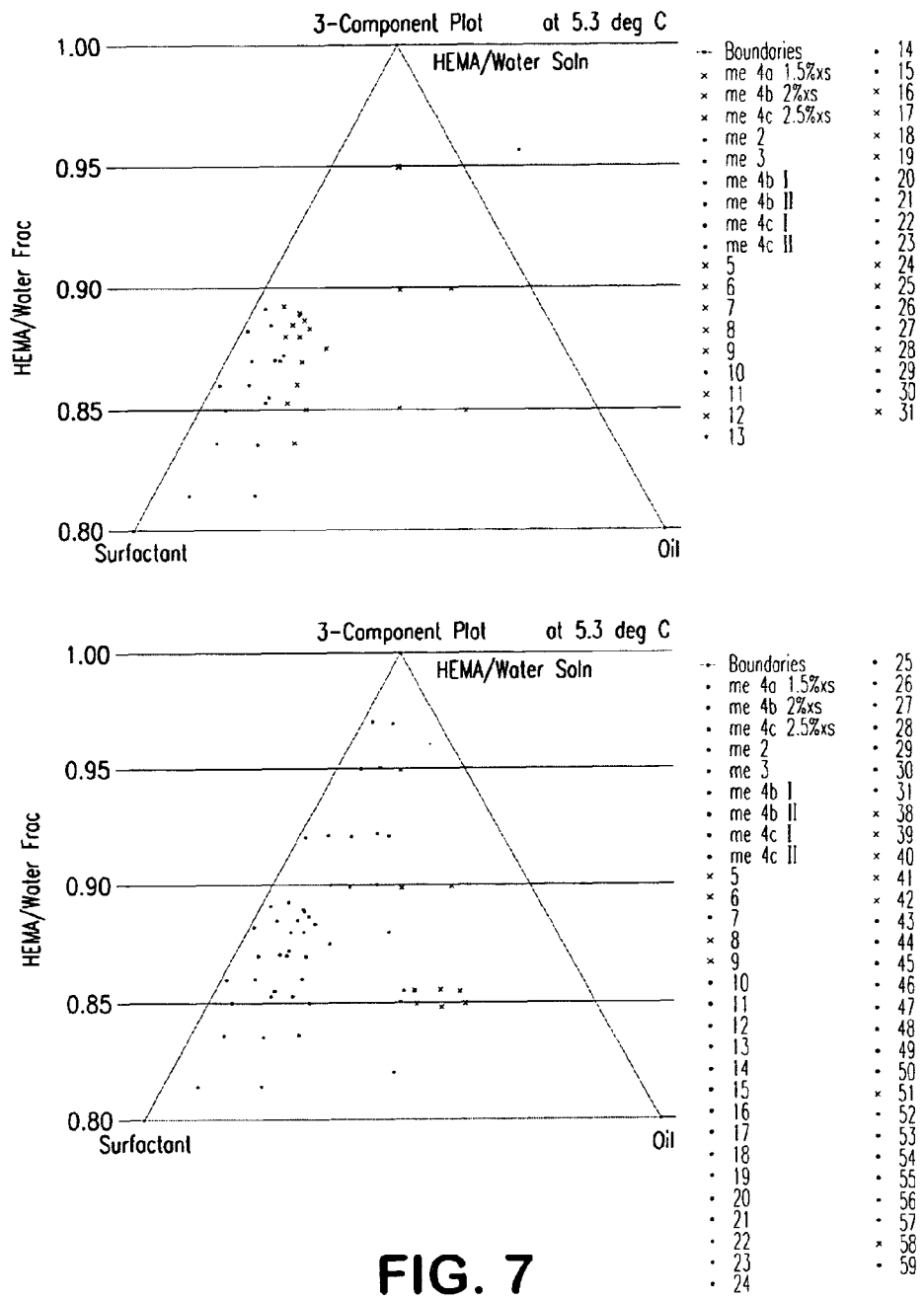
FIG. 7 is a phase diagram of an embodiment of the invention.

The rapid release in PBS could be due to a number of different reasons. First, the solubility of timolol is much larger in PBS than in DI water, and thus it is expected that the transport of the drug in gel will be faster if the gel is soaked in PBS or saline. Second, the microemulsions may be getting destabilized in PBS and saline, leading to a rapid release. To eliminate the second issue listed above, and also to minimize possible microemulsion destabilization during the gel polymerization, it was decided to synthesize microemulsion in HEMA-water solutions, and then polymerize the continuous phase of the microemulsions. However, ethyl butyrate which is the oil phase in the microemulsions is highly soluble In HEMA-water mix. In order to minimize the solubility of the oil in the continuous phase, it was decided to form the Pluronic microemulsions at a high pH and with salt added to the continuous phase. So these microemulsions contain six components which are water, NaCl, NaOH, HEMA, Ethyl butyrate, and F 127. The procedure used to prepare these microemulsions is essentially identical to that described above for synthesizing ethyl butyrate in water microemulsions. The major difference is that the water phase was replaced by a mixture of water, HEMA, NaOH and NaCl. Several experiments were conducted to determine the suitable ratios of these four components. The composition of the continuous phase was eventually fixed to be HEMA/$H_2O$/NaCl/(2N NaOH solution)=53.6:35.8:1.6:9. The fraction of oil and the surfactants was varied to investigate the compositions at which microemulsions form. The phase behavior of these 6 component systems was investigated at two different temperatures. The compositions explored in these experiments are indicated in the phase diagrams shown in FIGS. 7 *a-b* (Pseudo phase diagrams for the six component microemulsion at (a) room temperature and (b) 5° C.).

In all of these figures a 'X' mark indicates phase separation, and a 'O' marks formation of a single phase microemulsion. It was then decided to add timolol to a few of these compositions, polymerize the system into 200 μm thick gels, and then measure the drug release rates. After polymerizing the microemulsions, drug release studies were conducted both in PBS and in DI water with protocols identical to those described above. These experiments showed that these systems also had a very rapid release in PBS and a slow release in DI water. These results therefore eliminated the destruction of the microemulsions, or reduction in the packing at the interface as potential reasons for the vast differences between the release rates in DI water and in PBS.

The rapid release of timolol from these systems makes them unsuitable for contact lens applications. However it is very encouraging that these systems have a very large timolol loading, and if the release from these systems can be slowed down by increasing the interfacial packing, these systems could potentially be very useful.

Example 7

Synthesis of Cyclosporin Loaded Pluronic Microemulsion-laden Gels

The results of timolol release from hydro gels laden with drug-loaded Pluronic microemulsions in saline suggests that the surfactant covered interface of the drops offers negligible resistance to transport of solutes of the size of timolol. In order to determine the effect of molecular weight on the resistance offered by the microemulsion interface, it was decided to entrap cyclosporine (Mol weight 1202.6) into the Pluronic microemulsions, and then study the drug release from the microemulsion laden gels.

To synthesize cyclosprorin loaded Pluronic microemulsions, the same procedures were followed as for synthesizing timolol loaded microemulsions except that cyclosporine was dissolved in the oil phase instead of the timolol base. Specifically, 1.2 g of Pluronic F127 and 0.0163 g of sodium caprylate were dissolved in 9 ml saline (0.85 wt % NaCl), and stirred at about 600 rpm at room temperature for a period of about 5 hours. Next, 0.2 gm of cyclosporine was dissolved in 3 ml of ethyl butyrate and 100 μl of this solution was added to 5 ml of the surfactant solution, and stirred the above solution at 600 rpm at room temperature. After about 3 hours, the solution turned clear which indicated microemulsion formation. After microemulsion synthesis, gels loaded with cyclosporine containing microemulsions were prepared by following the same procedures as described previously for synthesis of gels loaded with timolol containing microemulsions.

Example 8

Cyclosporin Release from Pluronic Microemulsion-laden Gels in PBS

Figure 8:
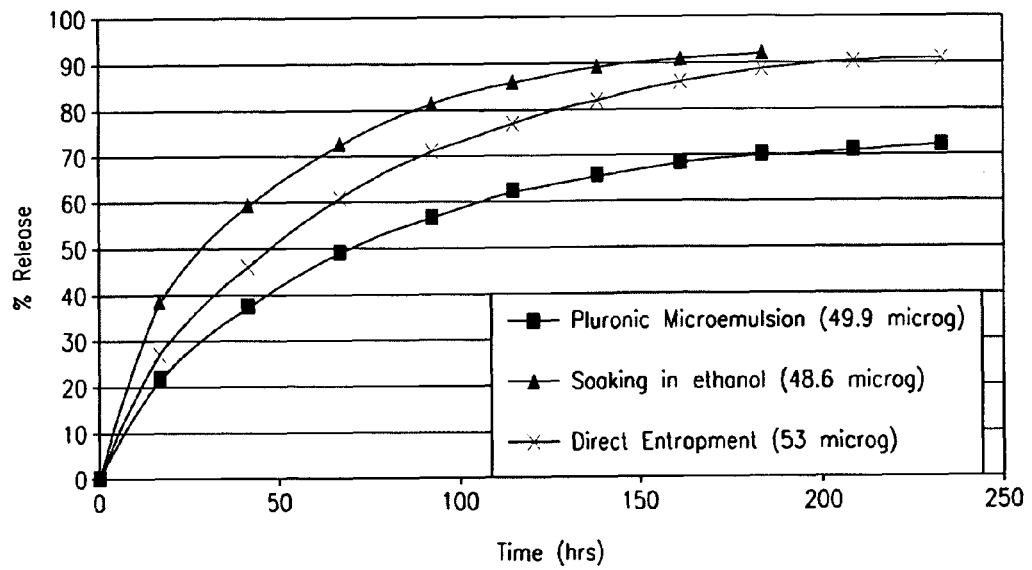
FIGS. 8-16 depict drug release rates for several embodiments of the invention.

Cyclosporin release from Pluronic microemulsion-laden gels were conducted by soaking a 50 mg of gel samples in 3 ml PBS and replacing the PBS every 24 hours. An extraction step was not performed in these experiments. For comparison, pure HEMA gels were loaded with the same amount of drug as the microemulsion-laden gels, and cyclosporine release was also performed from these gels. In these experiments, the concentration of cyclosporine was measured using a $C_{18}$ reverse phase column maintained at 60° C. in a High Performance Liquid Chromatography (Waters). The mobile phase composition was 70% acetonitrile and 30% DI water. The flow rate was maintained at 1.2 mL/min and the detection wavelength was set at 210 nm. Retention time for CyA was 4.5 minutes and was unaffected by entrapment of drug in the gels. The results of these studies are shown in FIG. 8, which is a comparison of cyclosporine release from Pluronic-microemulsion laden gels and HEMA gels. Cyclosporin (CyA) was loaded into the HEMA gels by direct drug addition to the polymerizing mixture (direct entrapment) and by soaking the HEMA gel in a solution of drug in ethanol. The amounts in parentheses represent the amount of CyA in the gels.

As shown in the figure, there are some differences between drug releases from HEMA gels and those from the microemulsion-laden gels. At short times, the HEMA gels release more drug compared to the microemulsion-laden gels, perhaps due to the presence of the microemulsion. But as time progresses there is a small amount of drug remaining in the HEMA gels, and so release rates become larger for the microemulsion-laden gels. These results suggest that due to increase in size, cyclosporine transport is hindered by the surfactant present on the interface of the microemulsion drops. However the resistance is perhaps small, and thus there is only a minor slow down in drug release rates due to the presence of the microemulsion.

Microemulsions using another class of surfactants, Brij surfactants were prepared. Brij surfactants are linear and so these are expected to pack effectively at the interface providing a larger resistance to drug transport. The studies on preparation of these microemulsions, fabrication of gels loaded with Brij microemulsions, and drug release studies are described below.

Example 9

Synthesis of Brij Based Microemulsions

To prepare the Brij microemulsion, 1 g of Brij 97 surfactant was dissolved in 10 ml of DI water and then stirred at about 600 rpm at room temperature for a period of about 10 hours. Separately 0.4 g of CyA was dissolved in 5 ml of ethyl butyrate, and 100 μl of this solution was added to 5 ml of the surfactant solution. The mixture was then stirred at 600 rpm for 20 minutes at 70° C. The mixture was then cooled to room temperature to form the microemulsion. The amount of surfactant added to 10 ml of DI water was increased to 1.5 and 2 g to obtain microemulsions with a higher surfactant loading.

Procedure for synthesis of CyA loaded Brij microemulsion gels. The procedure for synthesizing gels loaded with cyclosporine containing Brij microemulsions are identical to those used to load timolol containing microemulsions into the gel. Specifically, 2.7 ml of HEMA monomer was mixed with 15 μl of the crosslinker (EGDMA) and 2 ml of the cyclosporine containing Brij microemulsion. The solution was then degassed by bubbling nitrogen for 10 minutes. Next, 6 mg of the initiator (TPO) was added and the solution was stirred at 300 rpm for 10 minutes to ensure complete dissolution of the initiator. The mixture was then poured in between two glass plates that were separated from each other by a 200/lm thick spacer. The thickness of the spacer was reduced to 100 μm to fabricate thinner gels. The polymerization reaction was performed under UV light for 40 minutes. The gels fabricated by following the procedures described above had 5.6% of surfactant in the dry state. Gels were also prepared with 8% and 9.4% surfactant loading by increasing the amount of surfactant in the microemulsion. To synthesize HEMA gels without microemulsions, 2 ml of the microemulsion was replaced by 2 ml DI water, and the drug was directly added to the mixture of HEMA, EGDMA and DI water.

Example 10

Effect of Brij Microemulsions on Drug Release Profiles

Figure 9:
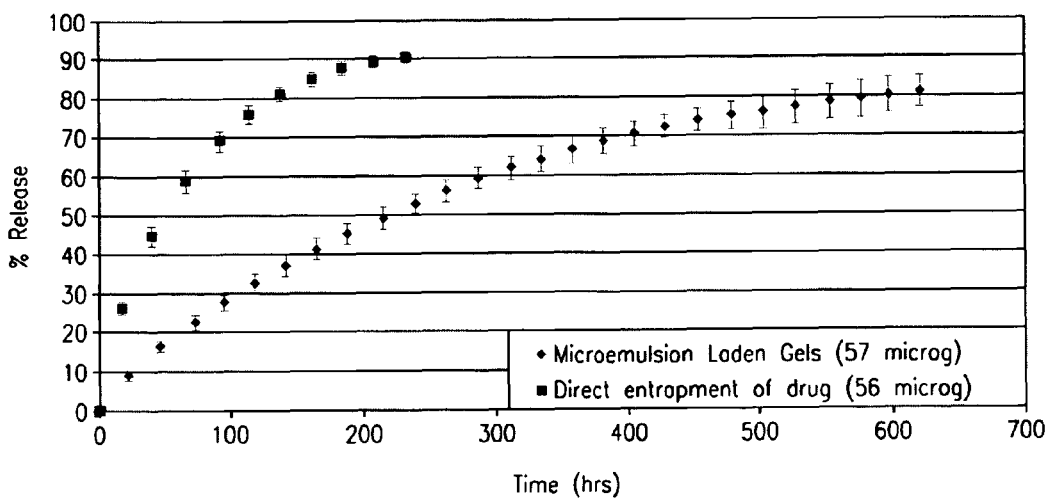

The drug release studies reported below were conducted with similar protocols as used while studying timolol release from Pluronic microemulsion-laden gels. Briefly, a 50 mg gel was soaked in 3.5 ml PBS and the PBS was replaced every 24 hours. An extraction step was not performed in these experiments. For comparison pure HEMA gels were loaded with the same amount of drug as the microemulsion-laden gels, and cyclosporine release was also performed from these gels. The release of cyclosporine from pure HEMA gels and that from the Brij microemulsion-laden gels with 8% surfactant loading (based on weight of surfactant in dry gel) is shown in FIG. 9 [Effect of microemulsion on cyclosporine release from HEMA gels. Drug was added to the microemulsion by dissolving it in the oil, and was added to the HEMA gels by adding it to the polymerizing mixture. The gels used in this study were 200 µm thick in dry state. The mass of drug in each gel is indicated in the figure captions in parentheses. The cyclosporin release from HEMA gels last only about 6-7 days but the microemulsion-laden gels release drug for about 25 days. This clearly demonstrates a significant reduction in delivery rate and an increase in the duration of release on addition of microemulsion to the gels.

Example 11

Dependence of the Release Rates on the Surfactant Loading

As stated above, the results shown in FIG. (9) are for a system that had 8% surfactant loading in the dry gel. To investigate the effect of the surfactant loading in the microemulsion on the drug release rates, it was decided to synthesize microemulsions with different surfactant loadings, and then entrap these in gels. By varying the amount of surfactant in the microemulsion, gels were synthesized with different amounts of surfactant and slightly different amounts of oil. Table 3 shows the weight percentages of surfactant, oil and cyclosporine in dry gels for the three compositions investigated in this study.

TABLE 3

Surfactant, oil and drug loadings for the three different Brij-microemulsion systems explored in this study

| | Brij 97 | Ethyl Butyrate | CyA |
|---|---|---|---|
| Surfactant 1 | 5.6% | 1% | 0.08% |
| Surfactant 2 | 8% | 1.2% | 0.09% |
| Surfactant 3 | 9.4% | 1.1% | 0.09% |

Example 12

Figure 10:
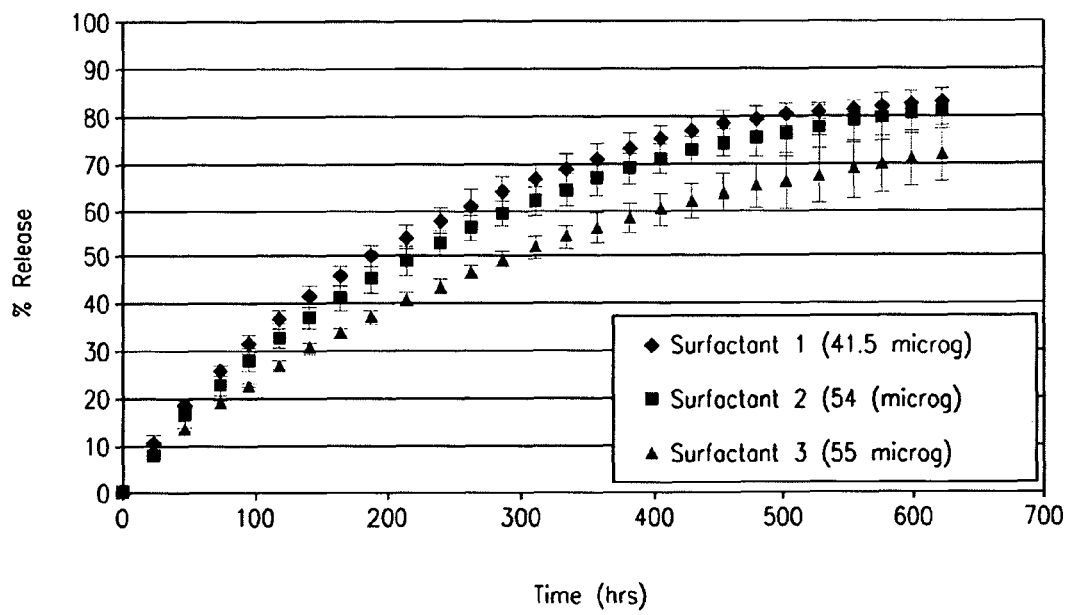

Drug release experiments were performed on these three gels with protocols described above, and the results are compared above in FIG. 10 [Effect of surfactant loading on cyclosporine release from microemulsion-laden gels. The compositions of the three systems are listed in Table 4. The gels used in this study were 200 µm thick in dry state. The mass of drug in each gel is indicated in the figure captions in parentheses].

Figure 11:
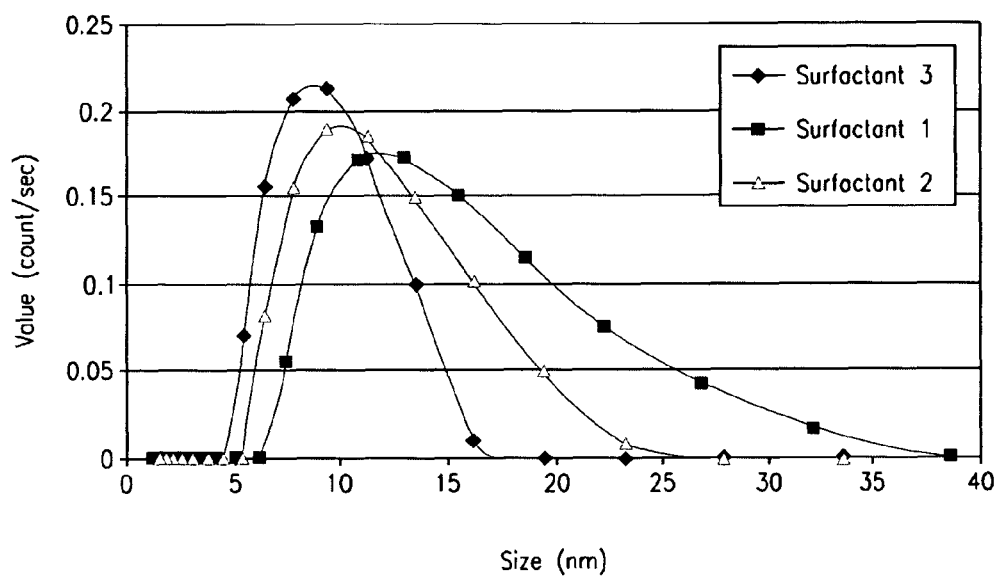

It was observed that the release rates decrease with an increase in surfactant concentration but the effect is minor. The reductions in release rates may be due an increased packing of surfactant at the surface of the microemulsions but the effect may be minor because the drop size in microemulsions decrease with an increasing surfactant concentration (see FIG. 11), and so the increase in total interfacial area may balance the increase in surfactant amount leading to minor changes in packing at the interface. It should be noted that the size distributions shown in FIG. 11 [Size distribution of microemulsion systems with three different surfactant loadings] were measured before addition of HEMA, and the drop size distributions may be different after the HEMA addition.

Example 13

Loading of Drug into the Gel by Soaking Microemulsion-laden Gels in Drug Solution In the experiments described above, cyclosporine was loaded by dissolving it into the oil phase of the microemulsion. It is conceivable that the process of gel formation may lead to partial loss of drug activity. It is noted that the elusion time of the drug in the HPLC did not change after gel entrapment but there still may be some loss of activity.

To eliminate the possible loss of activity due to the polymerization process, it was decided to conduct experiments in which the microemulsions (without drug) were entrapped in the gel, and the drug was loaded by soaking the gels into aqueous drug solutions. Specifically, drug was loaded by soaking the gels in 4 ml of drug solution where concentration of Cy A in the water phase was 11.5 µg/ml. The systems explored here had 7.25% Brij 97 and 1.2% Ethyl butyrate in the dry gel.

To determine the time needed for update of drug by the microemulsion-laden gels, the duration of soaking period was varied from 5, 10 and 15 days. After the soaking phase, the gels were withdrawn and the concentration of drug in the aqueous phase was measured. The mass of drug taken up by the gels was determined by subtracting the mass of drug left in the solution from the initial mass of drug in the soaking solution. Table 4 lists the amounts of drug that were taken up by the gels for the different soaking durations.

TABLE 4

Summary of drug uptake by Brij-microemulsion gels during soaking

| Duration of soaking (Days) | Initial amount of CyA In solution (µg) | Final amount of CyA solution (µg) | Amount of CyA taken up by the system (µg) |
|---|---|---|---|
| 5 | 46 | 16.2 | 29.8 |
| 10 | 46 | 15.1 | 30.9 |
| 15 | 46 | 15.2 | 30.8 |

Figure 12:
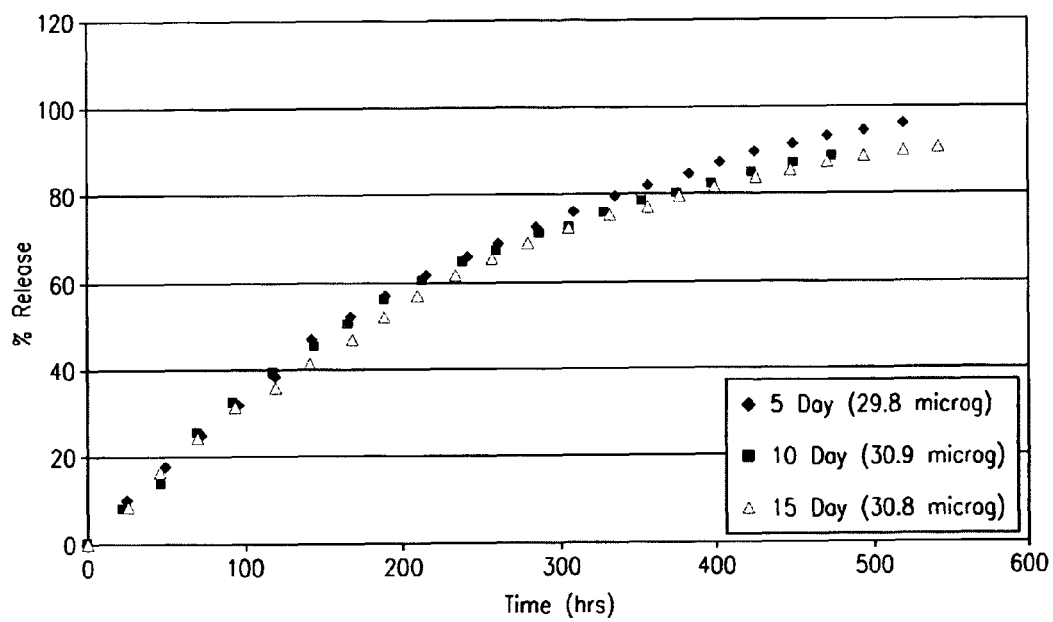

The results in Table 4 show that the mass drug of the drug taken up by the gels is relatively similar for all three gels. This shows that 5 says of soaking time is sufficient to establish equilibrium. Next, the gels were soaked in flesh PBS solution (3.5 ml) for the release experiments. During the release phase, PBS was changed every 24 hours. The results for the drug release are shown in FIG. 12 [Drug release from microemulsion gels in which drug was loaded after gel synthesis by soaking the gel in a drug solution (11.5 g drug/ml of water) for 5, 10 and 15 days. The gels used in this study were 200 µm thick in dry state. The mass of drug in each gel is indicated in the figure captions in parentheses].

The drug release profiles are relatively similar for the three gels. This is expected because the amount of drug taken by each of the gels was similar. These results also show that the duration of drug release for the systems in which the drug is loaded by soaking is same as that for the systems in which the drug is entrapped in the microemulsions.

Example 14

Effect of Packaging and 'Shelf Life' on Drug Release

To explore the effect of shelf life on drug release from the systems described above, it was decided to soak the drug containing microemulsion laden gels in 1.5 ml of 'packaging solution' for certain duration and then conduct drug release studies on the gel. The duration of soaking in packaging solutions was varied from 10-100 days. Also three different compositions of packaging solutions were explored. The first packaging medium was simply DI water, and the second and the third were 0.85% and 4.25% w/w salt solutions, respectively. The amounts of drug that diffused out into the packaging solutions are listed below.

TABLE 5

Summary of drug released during soaking from Brij microemulsion laden gels

| | Packaging Duration (days) | Initial Drug loading in gel (µg) | Drug release in the packaging medium (µg) | Drug left In the gel (µg) |
|---|---|---|---|---|
| Solution I | 10 | 44.2 | 7.1 | 37.1 |
| | 30 | 49.8 | 9.7 | 40.1 |
| | 100 | 46.9 | 17.6 | 29.3 |
| Solution II | 10 | 49.8 | 6.7 | 43.1 |
| | 30 | 47.7 | 10.3 | 37.4 |
| | 100 | 47.9 | 16.6 | 31.3 |
| Solution III | 10 | 52.3 | 3.3 | 48 |
| | 30 | 47.9 | 5.6 | 42.3 |
| | 100 | 52.6 | 9.6 | 43 |

The amount of drug that diffuses out of the gel is less for salt solutions because cyclosporine is a hydrophobic drug and so increasing ionic strength reduces drug solubility. Also, the amount of drug released into the packaging solution is largest for 100 day soak which shows that these systems take more than 30 days to equilibrate, which is consistent with the drug release studies.

Figure 13:
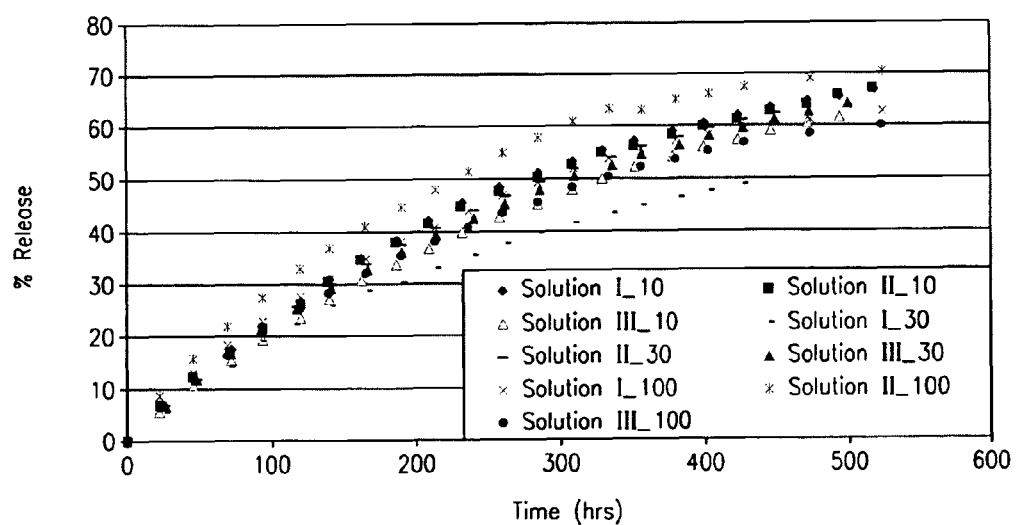

After the end of the packaging phase, the gels were withdrawn and drug release experiments were conducted with the usual protocols. The results of the drug release studies are shown in FIG. 13 [Drug release from Brij microemulsion-laden gels after they were soaked in three different 'packaging' solutions for three different durations. The gels used in this study were 200 µm thick in dry state]. These results demonstrate that the drug release profiles are relatively unaffected by soaking in packaging solution. Thus, contact lenses made of these types of gels can have extended shelf life.

Example 15

Effect of Gel Thickness on Drug Release Profiles

Figure 14:
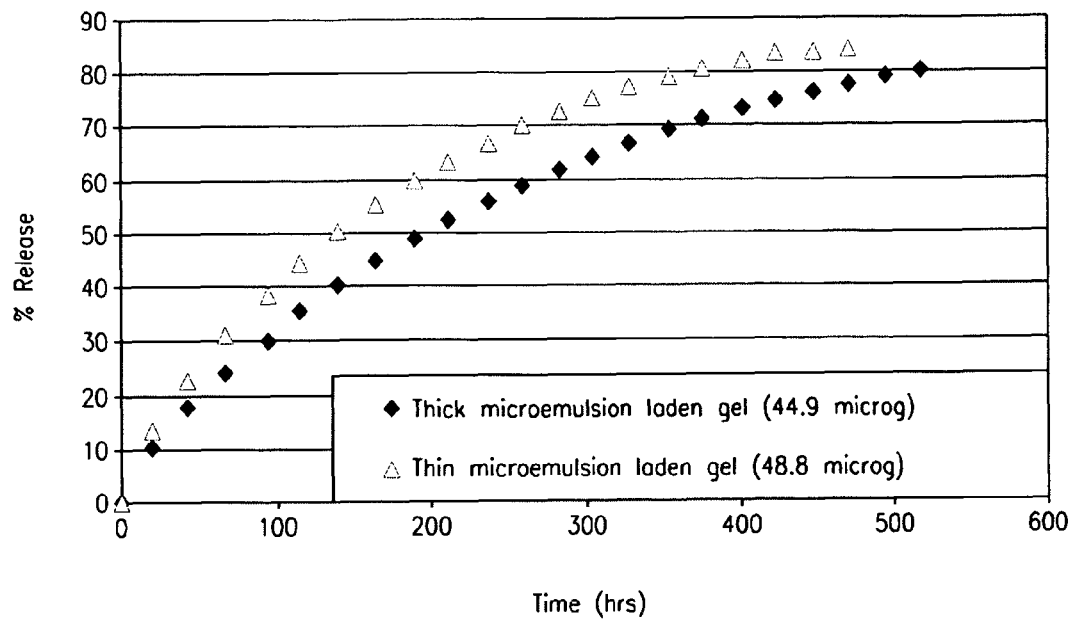
Figure 15:
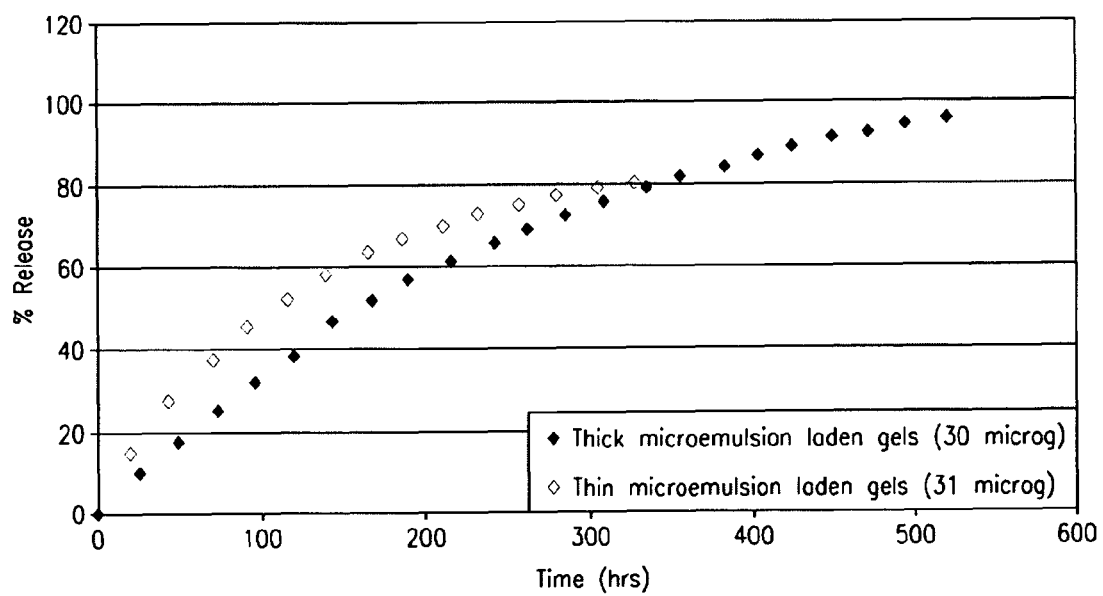

The results presented above were obtained with 200 µm thick gels. Typical contact lenses are about 100 µm thick, and so it was decided to explore the effect of gel thickness on release profiles. To explore this issue, two different sets of drug containing microemulsion-laden gels were synthesized. One set of these gels were about 200 µm thick and the others were about 100 µm thick. The drug was loaded into the gels by dissolving it in the oil phase of the microemulsion for one set of experiments and by soaking the microemulsion-laden gel in aqueous drug solutions for another set. Drug release experiments were conducted for both sets of these gels and the results are shown in FIG. 14 [Effect of gel thickness on drug release from microemulsion-laden gels. Drug was loaded in these gels by dissolving it in the oil phase. The mass of drug in each gel is indicated in parentheses in the captions] and FIG. 15 [Effect of gel thickness on drug release from microemulsion-laden gels. Drug was loaded in these gels by soaking the g drug/ml of water) for 5 days. The mass of drug□gels in a drug solution (11.5 in each gel is indicated in parenthesis in the captions]. It is noted that the weights of both the thick and then thin gels were about same because the cross sectional area of the thin gel was double that of the thick gel. As shown in the figures, the release rates are slightly smaller for the thick gels for both methods of drug loading, but the effect is minor. If the drug release profiles were controlled by diffusion, a change in thickness by a factor of 2 would lead to a four fold reduction in release time. Since we clearly do not observe a four fold reduction in the release duration, it can be concluded that the drug release process is not controlled by diffusion through the gel but by other processes such as transport across the surfactant covered interface of the microemulsions. Furthermore, since the release profiles are unaffected by thickness, it is expected that all the results shown above for 200 µm thick gels will be similar to those for 100 µm thick contact lenses.

Example 16

Effect of Processing Conditions on Drug Release

In order to evaluate the suitability of the Brij 97 microemulsion laden gels as contact lenses, gels were fabricated with the same thickness as contact lenses, and taken through processing conditions very similar to those used for typical contact lenses. Below the results of these studies are described.

(1) Synthesis: The synthesis procedures were identical to those described earlier for preparing Brij 97 microemulsion-laden gels. The gels used in these studies were about 100 µm thick and did not contain any drug. The drug was loaded later by soaking the gels in aqueous drug solutions.

(2) Extraction: The unreacted monomer was extracted from the gels by soaking gels that weighed about 40 mg in 10 ml of water at 50° C. The DI water was replaced every 5 minutes for 5 times. So the total duration for the extraction step was 25 minutes.

(3) Drug Loading: After extraction, each gel was soaked in 4 ml of cyclosporine solution in DI water at a concentration of 12 µg/ml for a period of 12 days. At the end of the loading phase, the concentration in the solution was measured. The drug uptake by the gel was then determined by calculating the difference between the initial and the final drug amounts in the solution. The results for the drug loaded into two sets of controls (pure HEMA gels) and two sets of microemulsion-laden gels are shown in Table 6. As shown in the Table, the microemulsion-laden gels take up more drug than the controls.

(4) Autoclaving: After drug loading, each gel was soaked in 1.5 ml of DI water and autoclaved for 15 min at 121° C.

(5) Shelf storage: After autoclaving, the samples were stored at room temperature for a period of 10 days. After the 10 day period, the concentration in the aqueous phase was measured to determine the amount of drug that was released from the gel during the autoclaving and shelf storage. By subtracting this amount from the amount of drug taken up by the gel, the remaining amount of drug left in the gel was determined. The results for the drug left in the gels after the storage are shown in Table 7. As shown in the Table, the microemulsion-laden gels retain much more drug than the controls.

(6) Drug release: In the final step, each gel was submerged in 3.5 ml of PBS, which was replaced every 24 hours, and the concentration of the drug was measured by HPLC. The elusion time of cyclosporine that diffused out of the gels after autoclaving was compared with the control to ensure that the drug did not degrade during the processing steps.

TABLE 6

Drug uptake by microemulsion-laden gels during soaking

| Sample | Drug in solution initially (µg) | Drug remaining in the solution after 12 days (µg) | Amount of drug inside the gel system (µg) |
|---|---|---|---|
| PureHEMA1 | 48 | 31.8 | 16.2 |
| PureHEMA2 | 48 | 27.1 | 20.9 |
| Microemulsion1 | 48 | 22 | 26 |
| Microemulsion2 | 48 | 22.9 | 25.1 |

TABLE 7

Summary of drug release studies from Brij-microemulsion laden gels

| Sample | Amount of drug inside the gel system before autoclaving (µg) | Amount of drug released during shelf storage (µg) | Amount of drug remaining inside the gel (µg) | Cumulative release during drug release phase (µg) |
|---|---|---|---|---|
| PureHEMA1 | 16.2 | 6.2 | 10 | 6.8 |
| PureHEMA2 | 20.9 | 6.2 | 14.7 | 5.6 |
| Microemulsion1 | 26 | 6.6 | 19.4 | 19.5 |
| Microemulsion2 | 25.1 | 6.4 | 18.7 | 19.3 |

Figure 16:
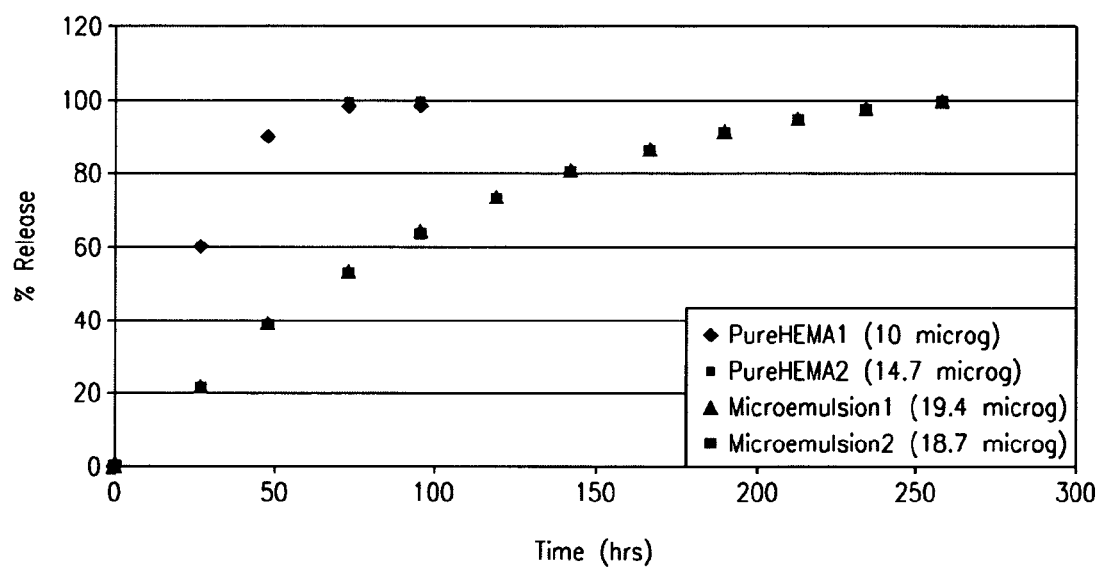

The drug release profiles for the cumulative release as a function of time are plotted in FIG. 16 [Comparison between pure HEMA gels and the microemulsion laden gels. Drug was loaded in both the cases by dissolving the gel piece in a drug solution (12 µg of drug/ml of DI water). All the gels were 100 µm in thickness. The drug loading utilized in computing the % Release is based on the total amount of drug that diffused out from the gels. These values are slightly different than the initial loading for the microemulsion-laden gels but are significantly different for pure HEMA gels]. The % Release plotted in these figures is based on the total measured release and not on the initial loading. The measured cumulative release is in good agreement with the initial loading for the microemulsion-laden gels but is much less than the total expected loading for the HEMA gels (see Table 8). The differences may be due to an underestimation of the drug release into the packaging solution and/or soaking solution for HEMA gels. The underestimation may be caused due to drug adsorption on the vial surface and/or aggregation, and these are more likely for HEMA gels because the concentration of drug in aqueous phase is higher for HEMA compared to microemulsion gels due to lower drug uptake. These results are very encouraging because even after going through all the processing steps that a contact lens undergoes, these Brij microemulsion-laden gels release cyclosporine for 15 days at a rate of about 1 µg/day, which is about twice the therapeutic requirement. Since about 50% of the drug released by a contact lens is expected to enter cornea, release rates of 1 µg/day from contact lenses may be sufficient. In any case, the drug loading into the gels can be increased by simply increasing the drug concentration in the soaking solution.

It is noted that similar ideas could be used to create hydrophilic microemulsions in silicone contact lenses. Hydrophilic drugs can then be trapped and slowly released from these hydrophilic microemulsions in the silicone contact lenses.

Unless stated otherwise, all percentages expressed herein are by weight. The entire disclosures and contents of each reference, patent and patent application referred to above are expressly incorporated herein by reference.

The invention claimed is:

1. An ophthalmically bioactive agent delivery system comprising a contact lens having dispersed therein as an oil-in-water microemulsion, an ophthalmically bioactive agent encapsulated in the oil phase of the microemulsion, the oil phase comprising an ophthalmically acceptable material from which the agent is capable of diffusion into and migration through the contact lens and into the post-lens tear film when the contact lens is placed on the eye and wherein the microemulsion is stabilized by the presence of an ophthalmically acceptable surfactant with sufficient packing at the oil-water interface to attenuate the rate of diffusion into and migration of agent through the contact lens.

2. A bioactive agent delivery system of claim 1 wherein said contact lens comprises a polymer of at least one hydrophilic monomer.

3. A bioactive agent delivery system of claim 1 wherein said contact lens comprises a hydrophobic material.

4. A bioactive agent delivery system of claim 3 wherein said hydrophilic monomer is a methacrylic or acrylic acid, 2-hydroxyethylmethacrylate, 2-hydroxyethylacrylate, N-vinyl pyrrolidone, methacrylamide or N,N-dimethylacrylamide.

5. A bioactive agent delivery system of claim 4 wherein said hydrophilic monomer is an unsaturated carboxylic acid; acrylic substituted alcohol; vinyl lactam or acrylamide.

6. A bioactive agent delivery system of claim 3 wherein said hydrophobic material is selected from the group consisting of a silicone, silicone containing prepolymers and macromers, polydimethylsiloxane, pentamethyldisiloxanyl methylmethacrylate, tris(trimethylsiloxy)methacryloxy; propylsilane, methyldi(trimethylsiloxy)methacryloxymethyl silane, monomethacryloxypropyl terminated mono-n-butyl terminated polydimethylsiloxane, mono-(3-methacryloxy-2-hydroxypropyloxy)propyl terminated, mono-butyl terminated polydimethylsiloxane, bis-3-methacryloxy-2-hydroxypropyloxypropyl polydimethylsiloxanes, 3-methacryloxy-2-hydroxypropyloxy)propylbis(trimethylsiloxy) methylsilane, 3-[tris(trimethylsiloxy)silyl]propyl vinyl carbamate, and methyl methacrylate, ethylene glycol di-methacrylate, and mixtures thereof.

* * * * *

UNITED STATES PATENT AND TRADEMARK OFFICE
CERTIFICATE OF CORRECTION

| | | |
|---|---|---|
| PATENT NO. | : 8,071,121 B2 | Page 1 of 1 |
| APPLICATION NO. | : 11/896571 | |
| DATED | : December 6, 2011 | |
| INVENTOR(S) | : Chauhan et al. | |

It is certified that error appears in the above-identified patent and that said Letters Patent is hereby corrected as shown below:

Column 18, Line 54 – delete ";" after "tris(trimethylsiloxy)methacryloxy"

Signed and Sealed this
Thirty-first Day of January, 2012

David J. Kappos
*Director of the United States Patent and Trademark Office*